United States Patent [19]

Farge et al.

[11] 4,137,315
[45] Jan. 30, 1979

[54] DERIVATIVES OF 10-NITRO-7-OXO-7H-INDOLIZINO[7,6,5-DE]ISOQUINOLINE

[75] Inventors: Daniel Farge, Thiais; Yves Le Goff, Bretigny-sur-Orge; Gilbert Poiget, Thiais, all of France

[73] Assignee: Rhone-Poulenc Industries, Paris, France

[21] Appl. No.: 806,344

[22] Filed: Jun. 14, 1977

[30] Foreign Application Priority Data

Jun. 16, 1976 [FR] France .................................. 76 18232
Apr. 8, 1977 [FR] France .................................. 77 10763

[51] Int. Cl.² ................. C07D 471/14; A61K 31/475
[52] U.S. Cl. .............................. 424/248.56; 424/250; 424/258; 424/262; 544/58; 544/125; 544/361; 546/66; 546/48; 546/141
[58] Field of Search ................. 544/125; 260/268 PC, 260/288 CF; 424/248.56, 250, 258, 262

[56] References Cited

U.S. PATENT DOCUMENTS 4,053,300  10/1977  Farge et al. .................. 260/288 CF Primary Examiner—Henry R. Jiles
Assistant Examiner—R. W. Ramsuer
Attorney, Agent, or Firm—Stevens, Davis, Miller & Mosher

[57] ABSTRACT

Indolizino[7,6,5-de]isoquinoline derivatives of the general formula:

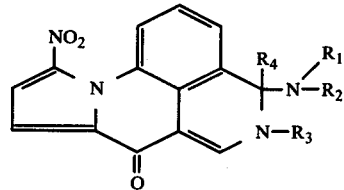

wherein the symbol $R_1$ represents a hydrogen atom, the symbol $R_2$ represents a hydrogen atom, an amino radical, or a straight- or branched-chain alkyl radical which is optionally substituted on a terminal carbon atom by a vinyl, ethynyl, carboxy, alkoxycarbonyl, cyano, dialkoxymethyl, hydroxymethyl, dialkylaminomethyl (the alkyl radicals of which may form with the nitrogen atom to which they are attached a saturated five- or six-membered heterocyclic ring which may contain another hetero-atom selected from nitrogen, oxygen and sulphur, and — when a second nitrogen atom is present — may optionally be N-methylated) or trialkylammoniomethyl radical, or $R_2$ represents a straight-chain alkyl radical which is substituted on the terminal carbon atom by an aminomethyl, alkylaminomethyl or hydroxyalkylaminomethyl radical, and the symbols $R_3$ and $R_4$ together form a valence bond, or the symbols $R_1$ and $R_4$ together form a valence bond and the symbols $R_2$ and $R_3$ together form a grouping of the general formula:

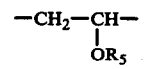

II wherein the group —$OR_5$, which represents an alkoxy radical, is attached to the carbon atom situated in the α-position to the nitrogen atom carrying $R_3$, the alkyl and alkoxy radicals, or moieties of groups, within the definition of symbols $R_2$ and $R_5$ containing from 1 to 4 carbon atoms and their salts are active as antimicrobial agents and antifungal agents, and are suitable for use as local antiseptics.

13 Claims, No Drawings

DERIVATIVES OF 10-NITRO-7-OXO-7H-INDOLIZINO[7,6,5-DE]ISOQUINOLINE

This invention relates to a new indolizino[7,6,5-de]isoquinoline derivatives, processes for their preparation and compositions containing them.

The indolizino[7,6,5-de]isoquinoline derivatives of the present invention are those compounds of the general formula:

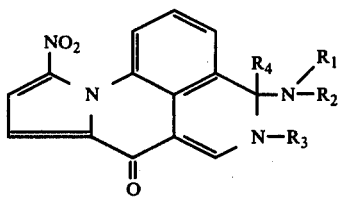

wherein the symbol $R_1$ represents a hydrogen atom, the symbol $R_2$ represents a hydrogen atom, an amino radical, or a straight- or branched-chain alkyl radical which is optionally substituted on a terminal carbon atom by a vinyl, ethynyl, carboxy, alkoxycarbonyl, cyano, dialkoxymethyl, hydroxymethyl, dialkylaminomethyl (the alkyl radicals of which may form with the nitrogen atom to which they are attached a saturated five- or six-membered heterocyclic ring which may contain another hetero-atom selected from nitrogen, oxygen and sulphur, e.g. piperidino, morpholino or piperazin-1-yl, which — when a second nitrogen atom is present — may optionally be N-methylated) or trialkylammoniomethyl radical, or $R_2$ represents a straight-chain alkyl radical which is substituted on the terminal carbon atom by an aminomethyl, alkylaminomethyl or hydroxyalkylaminomethyl radical, and the symbols $R_3$ and $R_4$ together form a valence bond, or the symbols $R_1$ and $R_4$ together form a valence bond and the symbols $R_2$ and $R_3$ together form a radical of the general formula:

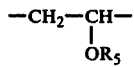

wherein the group —$OR_5$, which represents an alkoxy radical, is attached to the carbon atom situated in the α-position to the nitrogen atom carrying $R_3$, and — when appropriate - pharmaceutically acceptable salts thereof, viz, when $R_2$ represents a carboxyalkyl group their pharmaceutically acceptable metal salts, e.g. alkali metal and alkaline earth metal salts, ammonium salts and addition salts with nitrogen-containing bases, and pharmaceutically acceptable acid addition salts. It is to be understood that the alkyl and alkoxy radicals, or moieties of groups, within the definition of symbols $R_2$ and $R_5$ contain from 1 to 4 carbon atoms. It is to be understood that by the expression "a terminal carbon atom" as used in this specification and the accompanying claims is meant the terminal carbon atom of a straight-chain alkyl radical or one of the terminal carbon atoms of a branched-chain alkyl radical such as isopropyl or sec-butyl.

According to a feature of the invention, the compounds of general formula I, wherein $R_1$ represents a hydrogen atom, $R_2$ represents a hydrogen atom, an amino radical or a straight- or branched-chain alkyl radical which is optionally substituted on a terminal carbon atom by a vinyl, ethynyl, carboxy, alkoxycarbonyl, cyano, dialkoxymethyl, hydroxymethyl, dialkylaminomethyl (the alkyl radicals of which may form with the nitrogen atom to which they are attached a saturated five- or six-membered heterocyclic ring which may contain another hetero-atom selected from nitrogen, oxygen and sulphur, and may — when a second nitrogen atom is present — optionally be N-methylated) or trialkylammoniomethyl radical, or a straight-chain alkyl radical which is substituted on the terminal carbon atom by an aminomethyl, alkylaminomethyl or hydroxyalkylaminomethyl radical, and $R_3$ and $R_4$ together form a valence bond, are prepared by the process which comprises reacting a compound of the general formula:

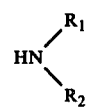

(wherein $R_1$ and $R_2$ are as defined above) with a 10-nitro-7-oxo-7H-indolizino[7,6,5-de]isoquinoline derivative of the general formula:

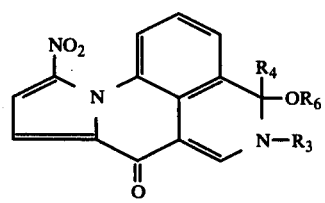

wherein $R_3$ and $R_4$ are as defined above and $R_6$ represents an alkyl radical containing 1 to 4 carbon atoms, preferably the ethyl radical, followed by isolation of the product of general formula I thus obtained.

The reaction is generally carried out at a temperature between 20° and 100° C., optionally in an organic solvent, such as pyridine or dimethylformamide. Isolation of the product is advantageously carried out by precipitation in water at a temperature of about 0° C.

The 10-nitro-7-oxo-7H-indolizino[7,6,5-de]isoquinoline derivatives of general formula IV can be obtained by nitrating the corresponding 7-oxo-7H-indolizino[7,6,5-de]isoquinoline of the general formula:

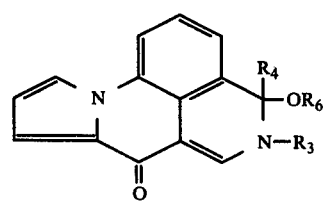

wherein $R_3$, $R_4$ and $R_6$ are as defined above. The nitration is generally carried out at a temperature between 0° and 10° C. using nitric acid of at least 50% by weight as the nitrating agent.

The 7-oxo-7H-indolizino[7,6,5-de]isoquinoline derivatives of general formula V can be prepared by the reaction of a tetrahydrofuran derivative of the general formula:

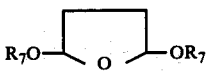

(wherein $R_7$ represents a methyl or ethyl radical) with a 5-amino-4-carboxyisoquinoline derivative of the general formula:

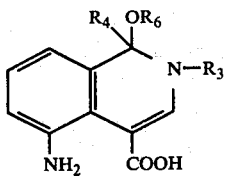

wherein $R_3$, $R_4$ and $R_6$ are as defined above. The reaction is generally carried out in an organic solvent, such as acetic acid, at a temperature between 90° and 100° C.

The 5-amino-4-carboxyisoquinoline derivatives of general formula VII can be prepared by reducing a 5-nitro-4-carboxyisoquinoline derivative of the general formula:

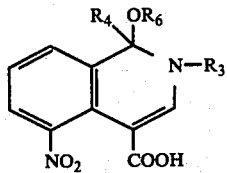

wherein $R_3$, $R_4$ and $R_6$ are as defined above. It is particularly advantageous to use sodium borohydride in the presence of palladium. The reaction is generally carried out under a nitrogen atmosphere, at a temperature between 20° and 30° C. and in an aqueous-alcoholic medium, such as a water-methanol mixture.

The 5-nitro-4-carboxyisoquinoline derivatives of general formula VIII can be prepared by nitrating a 4-carboxyisoquinoline derivative of the general formula:

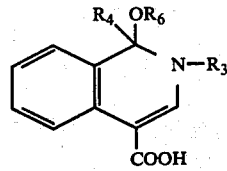

wherein $R_3$, $R_4$ and $R_6$ are as defined above. Potassium nitrate in concentrated sulphuric acid is advantageously used as the nitrating agent and the reaction is carried out at a temperature between 0° and 25° C.

The 4-carboxyisoquinoline derivatives of general formula IX can be prepared by reacting an alcohol of the general formula:

(wherein $R_6$ is as defined above) with 1-chloro-4-ethoxycarbonylisoquinoline in the presence of an alkali metal base, such as potassium hydroxide or sodium hydroxide. The reaction is advantageously carried out at the reflux temperature of the reaction mixture.

1-Chloro-4-ethoxycarbonylisoquinoline can be prepared according to the method described by M. D. Nair and P. A. Malik, Indian J. Chem., 10, 341 (1972).

According to another feature of the invention, the compounds of general formula I, wherein the symbols $R_1$ and $R_4$ together form a valence bond and the symbols $R_2$ and $R_3$ together form a grouping of general formula II, are prepared by the process which comprises cyclising, in an acid medium, a compound of general formula I wherein $R_1$ represents a hydrogen atom, $R_2$ represents the methyl radical which is substituted by a dialkoxymethyl radical and $R_3$ and $R_4$ together form a valence bond, that is to say starting from a compound of the general formula:

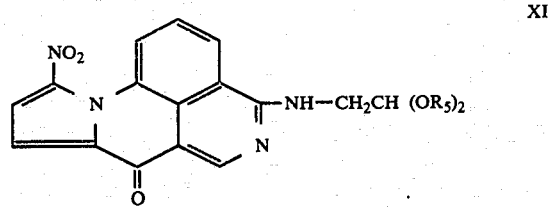

wherein $-OR_5$ is as hereinbefore defined.

The cyclisation is generally carried out in the presence of a strong inorganic acid in an organic solvent, such as acetic acid, and preferably at the reflux temperature of the reaction mixture.

According to still another feature of the invention, the compounds of general formula I, wherein the symbol $R_1$ represents a hydrogen atom, the symbol $R_2$ represents a straight- or branched-chain alkyl radical which is substituted on a terminal carbon atom by a trialkylammoniomethyl radical and the symbols $R_3$ and $R_4$ together form a valence bond, are prepared by the process which comprises reacting a reactive ester of the general formula:

(wherein R represents an alkyl radical containing 1 to 4 carbon atoms, and X represents the residue of a reactive ester such as a halogen atom or a sulphuric or sulphonic acid ester residue) with a compound of general formula I wherein $R_1$ represents a hydrogen atom, $R_2$ represents a straight- or branched-chain alkyl radical which is substituted on a terminal carbon atom by a dialkylaminomethyl radical and $R_3$ and $R_4$ together represent a valence bond.

The reaction is generally carried out in an organic solvent, such as acetone, acetonitrile or benzene, and at a temperature between 20° C. and the reflux temperature of the reaction mixture.

According to the present invention, the compounds of general formula I wherein $R_1$ represents a hydrogen atom, $R_2$ represents a straight- or branched-chain alkyl radical containing 1 to 4 carbon atoms which is substituted on a terminal carbon atom by a carboxy radical, and $R_3$ and $R_4$ together form a valence bond, are obtained by saponifying a compound of general formula I wherein $R_1$ represents a hydrogen atom, $R_2$ represents a straight- or branched-chain alkyl radical containing 1 to 4 carbon atoms which is substituted on a terminal carbon atom by an alkoxycarbonyl radical, and $R_3$ and $R_4$ together form a valence bond.

The saponification is generally carried out in an aqueous-alcoholic medium (e.g. water-ethanol) in the presence of sodium hydroxide or potassium hydroxide and at a temperature between 20° and 50° C.

According to the present invention, the compounds of general formula I, wherein $R_1$ represents a hydrogen atom, $R_2$ represents a straight- or branched-chain alkyl radical containing 1 to 4 carbon atoms, which is substituted on a terminal carbon atom by an alkoxycarbonyl radical, and $R_3$ and $R_4$ together form a valence bond, are obtained starting from a compound of general formula I wherein $R_1$ represents a hydrogen atom, $R_2$ represents a straight- or branched-chain alkyl radical containing 1 to 4 carbon atoms which is substituted on a terminal carbon atom by a carboxy radical, and $R_3$ and $R_4$ together form a valence bond, by methods known per se for converting a carboxy radical into an alkoxycarbonyl radical without affecting the rest of the molecule. By the term "methods known per se" as used in this specification is meant methods heretofore used or described in the chemical literature.

In order to convert the carboxy radical into an alkoxycarbonyl radical, it is particularly advantageous to carry out a direct esterification of the acid by means of an alcohol or to react an alkyl halide with an alkali metal salt of the acid or an ammonium salt of the acid. In order to prepare the methyl ester, it is also possible to react diazomethane with the acid.

The new indolizino[7,6,5-de]isoquinoline derivatives of general formula I obtained by the aforedescribed process can optionally be purified by physical methods, such as crystallisation or chromatography.

The compounds of general formula I can be converted by the application of methods known per se into acid addition salts. The acid addition salts can be obtained by the action of acids on the compounds of general formula I in appropriate solvents. As organic solvents there may be used alcohols, ketones, ethers or chlorinated hydrocarbons. The compounds of general formula I can be converted, where appropriate, into metal salts or addition salts with nitrogen-containing bases by the application of methods known per se. The metal salts and salts of nitrogen-containing bases can be obtained by the action of an alkali metal base or an alkaline earth metal base, of ammonia or of a nitrogen-containing base on an acid of general formula I wherein $R_2$ represents a carboxyalkyl radical in an appropriate solvent, such as an alcohol, an ether or water, or by an exchange reaction with a salt of an organic acid. The salt which forms is precipitated, if necessary after concentration of its solution, and is separated by filtration or decantation.

The compounds of general formula I and their pharmaceutically acceptable salts, are particularly active as antimicrobial agents and antifungal agents. Moreover, they have a very low toxicity.

The acute toxicity of the compounds has been principally studied in mice; it is between 750 mg/kg animal body weight and a dose greater than 1000 mg/kg animal body weight when administered orally.

They exhibit an in vitro activity against Grampositive bacteria. They have shown themselves to be active in concentrations between 0.008 and 2 μg/cc on Staphylococcus aureus 209 P. The majority of them also exhibit an in vitro activity against Gram-negative bacteria. They have shown themselves to be active in doses between 0.06 and 20 μg/cc against *Escherichia coli* of the Monod strain, at doses between 0.25 and 30 μg/cc against *Proteus vulgaris* and at doses between 2 and 60 μg/cc against *Pseudomonas aeruqinosa*.

As antifungal agents, they have shown themselves to be active, in particular, at doses between 1 and 125 μg/cc against *Saccharomyces pastorianus*.

The compounds of general formula I can be employed as such or - when appropriate - in the form of pharmaceutically acceptable salts, that is to say salts which are non-toxic to the animal organism at therapeutic doses of the salts.

Examples of suitable pharmaceutically acceptable salts are the salts with alkali metals (such as the potassium, sodium or lithium salt) or with alkaline earth metals, the ammonium salt, salts with nitrogen-containing bases (such as ethanolamine and lysine), and acid addition salts with inorganic or organic acids (such as hydrochlorides, sulphates, nitrates, phosphates, acetates, propionates, succinates, benzoates, fumarates, maleates, theophyllineacetates, salicylates, phenolphthalinates, methylene-bis-β-hydroxynaphthoates and methanesulphonates).

As the compounds of general formula I and their pharmaceutically acceptable salts are active on contact they are very suitable for use as local antiseptics. They can be used in dermatology, ophthalmology, gynaecology, urology, oto-rhino-laryngology, stomatology or in surgery.

Preferred compounds of general formula I are those wherein $R_1$ represents a hydrogen atom, $R_2$ represents a hydrogen atom or a straight- or branched-chain alkyl radical, e.g. methylene (—$CH_2$—), ethylene (—$CH_2CH_2$—) or ethylidene

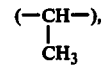

substituted on a terminal carbon atom by a carboxy, alkoxycarbonyl, dialkoxymethyl, hydroxymethyl, dialkylaminomethyl (the alkyl radicals of which may form with the nitrogen atom to which they are attached a saturated five- or six- membered heterocyclic ring, which may contain a second hetero-atom selected from nitrogen, oxygen and sulphur and may - when a second nitrogen atom is present - be optionally N-methylated, the heterocyclic ring preferably being piperidino, morpholino, piperazin-1-yl or 4-methylpiperazin-1-yl), or trialkylammoniomethyl radical, or $R_2$ represents a straight-chain alkyl radical which is substituted on the terminal carbon atom by a hydroxyalkylaminomethyl radical, and the symbols $R_3$ and $R_4$ together form a valence bond, or the symbols $R_1$ and $R_4$ together form a valence bond and the symbols $R_2$ and $R_3$ together form a grouping of formula II.

Of more particular interest are those compounds of general formula I wherein $R_1$ represents a hydrogen atom, $R_2$ represents a straight- or branched-chain alkyl radical which is substituted on a terminal carbon atom by a dialkylaminomethyl radical, the alkyl radicals of which may form with the nitrogen atom to which they are attached a saturated five- or six-membered heterocyclic ring as mentioned heretofore, or $R_2$ represents a straight-chain alkyl radical which is substituted on the terminal carbon atom by a hydroxyalkylaminomethyl radical, and $R_3$ and $R_4$ together form a valence bond.

Of outstanding interest are 4-(2-diethylaminoethylamino)-10-nitro-7-oxo-7H-indolizino[7,6,5-de]- isoquinoline, 4-[2-(2-hydroxyethylamino)ethylamino]-10-nitro-7-oxo-7H-indolizino[7,6,5-de]isoquinoline, 4-(3-dimethylaminopropylamino)-10-nitro-7-oxo-7H- indolizino[7,6,5-de]isoquinoline, 4-(2-dimethylamino-1-methylethylamino)-10-nitro-7-oxo-7H-indolizino[7,6,5-de]isoquinoline, 4-(2-morpholinoethylamino)-10-nitro-7-oxo-7H-indolizino[7,6,5-de]isoquinoline and 4-[2-(4-methylpiperazin-1-yl)ethylamino]-10-nitro-7-oxo-7H-indolizino[7,6,5-de]isoquinoline, and their pharmaceutically acceptable acid addition salts.

The following Examples illustrate the invention.

EXAMPLE 1

A stream of ammonia is passed into a solution of 4-ethoxy-10-nitro-7-oxo-7H-indolizino[7,6,5-de]isoquinoline (5 g) in pyridine (200 cc) until the solution is saturated. The solution obtained is then stirred at a temperature of about 20° C. for 16 hours. The resulting suspension of red crystals is poured into iced water (600 cc). The crystalline precipitate is filtered off and then washed successively with water (5 × 10 cc), ethanol (3 × 10 cc) and then diethyl ether (2 × 20 cc). After drying under reduced pressure (1 mm Hg) at 25° C., 4-amino-10-nitro-7-oxo-7H-indolizino[7,6,5-de]isoquinoline (4.18 g) is obtained in the form of orange-red crystals.

After recrystallisation from dimethylformamide (220 cc), the pure product melts, with decomposition, at 378° C.

4-Ethoxy-10-nitro-7-oxo-7H-indolizino[7,6,5-de]isoquinoline can be prepared in the following manner:

A mixture (150.4 cc) of equal volumes of about 50% by weight nitric acid (density 1.33) and about 97% by weight nitric acid (density 1.52) is added dropwise to a suspension, stirred and maintained between 5° and 10° C., of 4-ethoxy-7-oxo-7H-indolizino[7,6,5-de]isoquinoline (30 g) in nitric acid (density 1.33; 134 cc). The addition takes 15 minutes. The mixture is stirred for a further 15 minutes, whilst allowing the red solution to return to ambient temperature. This solution is poured into water (1.7 liter) and the orange solid which precipitates is filtered off. The residue is washed with water (5 × 50 cc) and then dried under reduced pressure (1 mm Hg) at 50° C. Crude 4-ethoxy-10-nitro-7-oxo-7H-indolizino[7,6,5-de]isoquinoline (31 g) is thus obtained. After recrystallisation from acetonitrile, the pure product melts at 192° C.

4-Ethoxy-7-oxo-7H-indolizino[7,6,5-de]isoquinoline can be prepared in the following manner:

A solution of 5-amino-4-carboxy-1-ethoxyisoquinoline (50.8 g) and 2,5-dimethoxytetrahydrofuran (32 cc) in acetic acid (250 cc) is kept at a temperature between 90° and 95° C. for 35 minutes, whilst stirring. The solution is cooled to about 20° C. and then poured into water (1250 cc). The yellow crystals which precipitate are filtered off and washed with water (5 × 50 cc). After drying under reduced pressure (1 mm Hg) at 20° C., crude 4-ethoxy-7-oxo-7H-indolizino[7,6,5-de]isoquinoline (52.7 g) is obtained. After recrystallisation from ethanol, the pure product melts at 188° C.

5-Amino-4-carboxy-1-ethoxyisoquinoline can be prepared in the following manner:

Palladium on charcoal (4.03 g) is added to a solution, stirred and kept under an atmosphere of nitrogen, of sodium borohydride (20.2 g) in water (700 cc). A solution of 4-carboxy-1-ethoxy-5-nitroisoquinoline (69.77 g) in methanol (700 cc) and N sodium hydroxide solution (293 cc) is run in dropwise into the suspension obtained during the course of 30 minutes.

The catalyst is subsequently filtered off and the methanol is evaporated under reduced pressure (25 mm Hg) at 40° C. Acetic acid (42 cc) is added all at once to the concentrate. The bulky solid precipitate which forms is filtered off and then washed with water (2 × 50 cc). After drying, 5-amino-4-carboxy-1-ethoxyisoquinoline (50.8 g), which melts at 159–165° C., is obtained.

4-Carboxy-1-ethoxy-5-nitroisoquinoline can be prepared in the following manner:

A solution of potassium nitrate (34.9 g) in sulphuric acid (density 1.83; 280 cc) is added dropwise to a solution, stirred and cooled by iced water, of 4-carboxy-1-ethoxyisoquinoline (69.5 g) in sulphuric acid (density 1.83; 420 cc), whilst keeping the temperature below 20° C. The reactants are kept in contact for 16 hours at a temperature of about 20° C. and the reaction solution is then poured onto crushed ice (7 kg). The fine yellow crystals which precipitate are filtered off and then washed with water until a neutral filtrate is obtained. After drying, crude 4-carboxy-1-ethoxy-5-nitroisoquinoline (84.5 g) is obtained.

The product, purified by recrystallisation from 90% aqueous ethanol, melts at 238° C.

1-Ethoxy-4-carboxyisoquinoline can be prepared in the following manner:

A suspension of 1-chloro-4-ethoxycarbonyliso-quinoline (76.9 g) in a solution of potassium hydroxide (97.3 g) in ethanol (769 cc) is boiled for 6 hours, whilst stirring. After cooling, the ethanol is evaporated under reduced pressure (20 mm Hg) at 25° C. and the solid residue is then taken up in water (1 liter). The solution obtained is filtered in order to remove traces of insoluble material and then acidified by adding concentrated hydrochloric acid (60 cc).

The white crystalline precipitate is filtered off, washed with water (3 × 100 cc), and then dried under reduced pressure (1 mm Hg) at 25° C. 1-Ethoxy-4-carboxyisoquinoline (65.7 g) is thus obtained which melts at 222° C. and then, after resolidifying, at 235° C.

1-Chloro-4-ethoxycarbonylisoquinoline can be prepared according to the process described by M. D. Nair and P. A. Malik, Indian J. Chem., 10, 341 (1972).

EXAMPLE 2

A solution of 4-ethoxy-10-nitro-7-oxo-7H-indolizino[7,6,5-de]isoquinoline (5 g) and of ethanolamine (10 cc) in pyridine (50 cc) is stirred at 50° C. for 1 hour. The dark red solution thus obtained is poured into iced water (300 cc) and the red crystals which precipitate are then filtered off. They are washed with water (3 × 10 cc) and then dried under reduced pressure (1 mm Hg) at 50° C.

Crude 4-(2-hydroxyethylamino)-10-nitro-7-oxo-7H-indolizino[7,6,5-de]isoquinoline (4 g) is thus obtained.

After recrystallisation from a mixture of pyridine (102 cc) and ethanol (55 cc), the pure product melts, with decomposition, at 218° C.

EXAMPLE 3

A solution of 4-ethoxy-10-nitro-7-oxo-7H-indolizino[7,6,5-de]isoquinoline (4.45 g) in N,N-diethylethylenediamine (67 cc) is stirred at a temperature of about 20° C. After stirring for 5 minutes, crystals are formed. The mixture is stirred for a further 40 minutes and the dark red suspension thus obtained is then poured into iced water (335 cc). After filtering off the crystals, they are washed with water (3 × 10 cc) and then dried under reduced pressure (1 mm Hg) at 50° C. Crude 4-(2-diethylaminoethylamino)-10-nitro-7-oxo- 7H-indolizino[7,6,5-de]isoquinoline (4.20 g) is thus obtained.

After recrystallisation from ethanol (176 cc), the pure product melts at 199° C.

EXAMPLE 4

A solution of 4-ethoxy-10-nitro-7-oxo-7H-indolizino[7,6,5-de]isoquinoline (7 g) in 2,2-dimethoxyethylamine (50 cc) is stirred at 60° C. Red crystals are rapidly formed. After stirring for 30 minutes, the dark red suspension obtained is poured into iced water (250 cc).

The deep red crystalline precipitate is filtered off and then washed with water (3 × 10 cc). After drying under reduced pressure (0.1 mm Hg) at 60° C., crude 4-(2,2-dimethoxyethylamino)-10-nitro-7-oxo-7H-indolizino[7,6,5-de]isoquinoline (6.1 g) is obtained.

After recrystallisation from dimethylformamide, the pure product melts, with decomposition, at 238° C.

EXAMPLE 5

A solution of 4-ethoxy-10-nitro-7-oxo-7H-indolizino[7,6,5-de]isoquinoline (9 g) and of ethyl 3-aminopropionate (9 g) in pyridine (90 cc) is stirred at 45° C. for 4 hours and then at ambient temperature for 16 hours. The intense red solution thus obtained is poured into iced water (540 cc).

The fine dark red solid which precipitates is filtered off and then washed with water (3 × 10 cc). After drying under reduced pressure (1 mm Hg) at 25° C., crude 4-(2-ethoxycarbonylethylamino)-10-nitro-7-oxo-7H-indolizino[7,6,5-de]isoquinoline (10.16 g) is obtained.

After chromatography on a silica column, the pure product melts at 230° C.

EXAMPLE 6

A mixture of 4-(2-ethoxycarbonylethylamino)-10-nitro-7-oxo-7H-indolizino[7,6,5-de]isoquinoline (3.8 g), water (38 cc), ethanol (20 cc) and N sodium hydroxide (10.5 cc) is stirred at 50° C. for 1 hour. The reaction medium is cooled by means of an ice-water bath and the orange-red solid product is filtered off and washed successively with ethanol (2 × 10 cc), acetone (4 × 25 cc) and then methylene chloride (4 × 25 cc).

After drying under reduced pressure (1 mm Hg) at 40° C., the sodium salt of 4-(2-carboxyethylamino)-10-nitro-7-oxo-7H-indolizino[7,6,5-de]isoquinoline (3.64 g) is obtained.

EXAMPLE 7

4-(2,2-Dimethoxyethylamino)-10-nitro-7-oxo-7H-indolizino[7,6,5-de]isoquinoline (3.68 g) is dissolved at the boiling point in acetic acid (74 cc), whilst stirring. Concentrated hydrochloric acid (7.4 cc) is added all at once to the solution thus obtained and the mixture is then kept at the reflux for a further 5 minutes. The yellow-brown solution is cooled to a temperature of about 20° C. and the solvents are then evaporated off under reduced pressure (20 mm Hg) at 25° C.

The orange-coloured crystalline residue is taken up in water (50 cc), and then filtered off and washed with water (3 × 5 cc). After drying, 6-methoxy-12-nitro-9-oxo-5,6-dihydro-7H-imidazo[2,1-a]indolizino[7,6,5-de]isoquinoline hydrochloride (3.26 g) which melts (with decomposition) at about 255-260° C., is obtained.

This product is suspended in a mixture of pyridine (16 cc) amd water (80 cc). The reactants are left in contact for 30 minutes and the red crystals are then filtered off, washed with water 5 × 5 cc) and then dried under reduced pressure (1 mm Hg). Crude 6-methoxy-12-nitro-9-oxo-5,6-dihydro-7H-imidazo[2,1-a]indolizino[7,6,5-de]isoquinoline (2.95 g) is thus obtained.

The product, purified by recrystallisation from pyridine, melts at 250° C.

EXAMPLE 8

4-(2-Diethylaminoethylamino)-10-nitro-7-oxo-7H-indolizino[7,6,5-de]isoquinoline (0.92 g) and dimethyl sulphate (0.306 g) are refluxed in acetone (30 cc), whilst stirring, until they are dissolved. The mixture is allowed to cool to a temperature of about 20° C. and is then stirred for 16 hours at this temperature.

The orange-coloured crystals which have separated out are filtered off, washed with acetone (3 × 2 cc) and then dried. 4-(2-Diethylmethylammonio-ethylamino)-10-nitro-7-oxo-7H-indolizino[7,6,5-de]isoquinoline methyl sulphate (1.15 g), which melts (with decomposition) at about 180° C., is thus obtained.

EXAMPLE 9

N-(2-Hydroxyethyl)ethylenediamine (1.77 g) is added all at once to a solution, stirred and heated to 70° C., of 4-ethoxy-10-nitro-7-oxo-7H-indolizino[7,6,5-de]isoquinoline (5 g) in dimethylformamide (200 cc). The red solution thus obtained is allowed to return to ambient temperature (about 20° C.) in the course of 2 hours. A suspension of red crystals is thus obtained, to which distilled water (200 cc) is added. The crystals are filtered off and then washed with water (3 × 10 cc). After drying under reduced pressure (1 mm Hg) at 24° C., brick-red crystals of crude 4-[2-(2-hydroxyethylamino)ethylamino]-10-nitro-7-oxo-7H-indolizino[7,6,5-de]isoquinoline (5.08 g) are obtained.

After recrystallisation from a mixture of dimethylformamide (50 cc) and ethanol (200 cc), the pure product melts (with decomposition) at 224° C.

EXAMPLE 10

Following a similar procedure to that described in Example 9 but starting with 4-ethoxy-10-nitro-7-oxo-7H-indolizino[7,6,5-de]isoquinoline (5 g) and 3-dimethylaminopropylamine (3.66 g), after 18 hours of contact crude 4-(3-dimethylaminopropylamino)-10-nitro-7-oxo-7H-indolizino[7,6,5-de]isoquinoline (4.9 g) is obtained.

After recrystallisation from isopropanol (330 cc), the pure product obtained in the form of bright red platelets melts at 219° C.

EXAMPLE 11

Following a similar procedure to that described in Example 9 but starting with 4-ethoxy-10-nitro-7-oxo-7H-indolizino[7,6,5-de]isoquinoline (5 g) and 2-morpholinoethylamine (4.78 g), after 20 hours of contact crude 4-(2-morpholinoethylamino)-10-nitro-7-oxo-7H-indolizino-[7,6,5-de]isoquinoline (5.90 g) is obtained.

After recrystallisation from a mixture of dimethylformamide (60 cc) and isopropanol (240 cc), the pure product obtained in the form of fine orange-coloured crystals melts at 240° C.

EXAMPLE 12

Following a similar procedure to that described in Example 9 but starting with 4-ethoxy-10-nitro-7-oxo-7H-indolizino[7,6,5-de]isoquinoline (5 g) and 2-amino-1- dimethylaminopropane (3.36 g), after 3 hours 30 minutes of contact crude 4-(2-dimethylamino-1-methylethylamino)-10-nitro-7-oxo-7H-indolizino[7,6,5-de]isoquinoline (5.51 g) is obtained.

After recrystallisation from isopropanol (212 cc), the pure product obtained in the form of red crystals melts (with decomposition) at 203° C.

EXAMPLE 13

Following a similar procedure to that described in Example 9 but starting with 4-ethoxy-10-nitro-7-oxo-7H-indolizino[7,6,5-de]isoquinoline (5 g) and 2-(4-methylpiperazin-1-yl)ethylamine (4.62 g), after 4 hours of contact crude 4-[2-(4-methylpiperazin-1-yl)ethylamino]-10-nitro-7-oxo-7H-indolizino[7,6,5-de]isoquinoline (6 g) is obtained.

After recrystallisation from ethanol (300 cc), the pure product obtained in the form of fine red-orange crystals melts at 224° C.

The present invention also includes within its scope medicinal compositions which comprise, as an active ingredient, a compound of general formula I, or a pharmaceutically acceptable salt thereof, in association with a diluent. The compositions can be used for local administration.

Liquid compositions for local administration are, most frequently, pharmaceutically acceptable emulsions, solutions and suspensions containing diluents such as water or alcohol. These compositions can also contain substances other than the diluents, for example wetting agents, colouring agents or perfumes.

Semi-solid compositions for local administration are usually ointments and creams. These compositions can contain, in addition to the antiseptic compound, wetting agents, colouring agents, perfumes, mineral salts, such as calcium carbonate or magnesium carbonate or tricalcium phosphate, and diluents, such as starch or talc.

Solid compositions for local administration are usually powders. These compositions can contain, in addition to the antiseptic compound, diluents, colouring agents or perfumes. The powders are generally used after being dissolved or suspended in a sterile liquid, such as water or alcohol, or directly by dusting.

In these compositions, the content of active compound is generally between 0.01% and 0.5% by weight.

The following Examples illustrate medicinal compositions according to the invention.

EXAMPLE 14

A solution containing 0.50% by weight of active compound and having the following composition is prepared by customary methods:

| | |
|---|---|
| 4-(2-diethylaminoethylamino)-10-nitro-7-oxo-7H-indolizino[7,6,5-de]isoquinoline methanesulphonate | 0.64 g |
| water | 100 ml. |

EXAMPLE 15

A cream containing 0.50% by weight of active compound and having the following composition is prepared by customary methods:

| | |
|---|---|
| 4-(2-hydroxyethylamino)-10-nitro-7-oxo-7H-indolizino[7,6,5-de]isoquinoline | 0.50 g |
| methyl and propyl p-hydroxybenzoates (75:25) | 0.01 g |
| excipient (lanolin, petroleum jelly) | 99.5 g |

EXAMPLE 16

A solution containing 0.50% by weight of active compound and having the following composition is prepared by customary methods:

| | |
|---|---|
| 4-[2-(2-hydroxyethylamino)ethylamino]-10-nitro-7-oxo-7H-indolizino[7,6,5-de]isoquinoline methanesulphonate | 0.64 g |
| water | 100 ml. |

We claim:
1. An indolizino[7,6,5-de]isoquinoline derivative of the general formula:

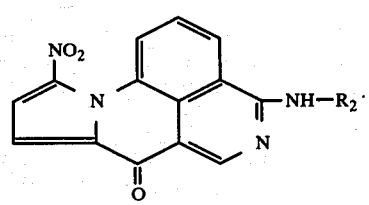

I wherein the symbol $R_2$ represents a hydrogen atom, an amino radical, or a straight- or branched-chain alkyl radical which is optionally substituted on a terminal carbon atom by a vinyl, ethynyl, dialkoxymethyl, hydroxymethyl, dialkylaminomethyl (the alkyl radicals of which may form with the nitrogen atom to which they are attached piperidino, morpholine, piperazin-1-yl or 4-methyl piperazin-1-yl or trialkylammoniomethyl radical, or $R_2$ represents a straight-chain alkyl radical which is substituted on the terminal carbon atom by an aminomethyl, alkylaminomethyl or hydroxyalkylaminomethyl radical, the alkyl and alkoxy radicals, or moieties of groups, within the definition of symbol $R_2$ containing from 1 to 4 carbon atoms, and - when appropriate - non-toxic pharmaceutically acceptable salts thereof.

2. An indolizino[7,6,5-de]isoquinoline derivative according to claim 1 wherein $R_2$ represents a hydrogen atom or a straight- or branched-chain alkyl radical substituted on a terminal carbon atom by a dialkoxymethyl, hydroxymethyl, dialkylaminomethyl (the alkyl radicals of which may form with the nitrogen atom to which they are attached piperidino, morpholins, piperazin-1-yl or 4-methyl-piperazin-1-yl or trialkylammoniomethyl radical, or $R_2$ represents a straight-chain alkyl radical which is substituted on the terminal carbon atom by a hydroxyalkylaminomethyl radical, and - when appropriate - non-toxic pharmaceutically acceptable salts thereof.

3. An indolizino[7,6,5-de]isoquinoline derivative according to claim 1 wherein $R_2$ represents a straight- or branched-chain alkyl radical which is substituted on a terminal carbon atom by a dialkylaminomethyl radical, the alkyl radicals of which may form with the nitrogen atom to which they are attached piperidino, morpholine, piperazin-1-yl or 4-methyl piperazin-1-yl or $R_2$ represents a straight-chain alkyl radical which is substituted on the terminal carbon atom by a hydroxyalkylaminomethyl radical, and - when appropriate - non-toxic pharmaceutically acceptable salts thereof.

4. An indolizino[7,6,5-de]isoquinoline derivative according to claim 1 wherein $R_2$ represents a hydrogen atom, an amino radical or a straight-chain alkyl radical which is optionally substituted on the terminal carbon atom by a vinyl, ethynyl, dialkoxymethyl, hydroxymethyl, aminomethyl, alkylaminomethyl, dialkylaminomethyl (the alkyl radicals of which may form with the nitrogen atom to which they are attached piperidino, morpholine, piperazin-l-yl or 4-methyl piperazin-l-yl or trialkylammoniomethyl radical, and - when appropriate - non-toxic pharmaceutically acceptable salts thereof.

5. An indolizino[7,6,5-de]isoquinoline derivative according to claim 1 wherein $R_2$ represents a straight-chain alkyl radical substituted on the terminal carbon atom by a hydroxyalkylaminomethyl radical, or represents a branched-chain alkyl radical optionally substituted on one of the terminal carbon atoms by a vinyl, ethynyl, dialkoxymethyl, hydroxymethyl, dialkylaminomethyl (the alkyl radicals of which may form with the nitrogen atom to which they are attached piperidino, morpholine piperazin-1-yl or 4-methyl piperazin-1-yl and - when appropriate - non-toxic pharmaceutically acceptable salts thereof.

6. An indolizino[7,6,5-de]isoquinoline derivative according to claim 1 wherein $R_2$ represents a straight- or branched-chain alkyl radical which is substituted on a terminal carbon atom by a piperidinomethyl, morpholinomethyl, piperazin-1ylmethyl or 4-methylpiperazin-1-ylmethyl radical, and - when appropriate - non-toxic pharmaceutically acceptable salts thereof.

7. The indolizino[7,6,5-de]isoquinoline derivative according to claim 1 which is 4(2-diethylaminoethylamino)-10-nitro-7-oxo-7$\underline{H}$-indolizino[7,6,5-de]isoquinoline and its non-toxic pharmaceutically acceptable acid addition salts.

8. The indolizino[7,6,5-de]isoquinoline derivative according to claim 1 which is 4-[2-(2-hydroxyethylamino)ethylamino]-10nitro-7-oxo-7$\underline{H}$-indolizino[7,6,5-de]isoquinoline and its non-toxic pharmaceutically acceptable acid addition salts.

9. The indolizino[7,6,5-de]isoquinoline derivative according to claim 1 which is 4-(3-dimethylaminopropylamino)10-nitro-7-oxo-7$\underline{H}$-indolizino[7,6,5-de]isoquinoline and its non-toxic pharmaceutically acceptable acid addition salts.

10. The indolizino[7,6,5-de]isoquinoline derivative according to claim 1 which is 4-(2-dimethylamino-1-methylethylamino)-10-nitro-7-oxo-7$\underline{H}$-indolizino[7,6,5-de]isoquinoline and its non-toxic pharmaceutically acceptable acid addition salts.

11. The indolizino[7,6,5-de]isoquinoline derivative according to claim 1 which is 4-(2-morpholinoethylamino)-10-nitro-7-oxo-7$\underline{H}$-indolizino[7,6,5-de]isoquinoline and its non-toxic pharmaceutically acceptable acid addition salts.

12. The indolizino[7,6,5-de]isoquinoline derivative according to claim 1 which is 4-[2-(4-methylpiperazin-1-yl)-ethylamino]-10-nitro-7-oxo-7$\underline{H}$-indolizino[7,6,5-de]isoquinoline and its non-toxic pharmaceutically acceptable acid addition salts.

13. A medicinal composition useful as an antimicrobial and antifungal agent which comprises an effective amount of an indolizino[7,6,5-de]isoquinoline derivative as claimed in claim 1, or - when appropriate - a non-toxic pharmaceutically acceptable salt thereof, in association with a suitable diluent.

* * * * *